US00PP10674P

United States Patent [19]

Pouw

[11] Patent Number: Plant 10,674

[45] Date of Patent: Nov. 10, 1998

[54] HYBRID TEA ROSE PLANT NAMED 'RUIORAN'

[75] Inventor: A. A. Pouw, De Kwakel, Netherlands

[73] Assignee: De Ruiter's Nieuwe Rozen B.V., Netherlands

[21] Appl. No.: 789,852

[22] Filed: Jan. 28, 1997

[51] Int. Cl.[6] ..... A01H 5/00

[52] U.S. Cl. ..... Plt./16

[58] Field of Search ..... Plt./11, 16, 17, Plt./15

*Primary Examiner*—Howard J. Locker

*Attorney, Agent, or Firm*—Christie, Parker & Hale, LLP

[57] ABSTRACT

A new variety of hybrid tea rose plant producing orange yellow flowers of good form and suitable for growing under glass.

2 Drawing Sheets

BACKGROUND OF THE INVENTION

The present invention relates to a new and distinct variety of rose plant of the hybrid tea rose class which was created by crossing undistributed, unnamed and unpatented seedlings as seed and pollen parents in De Kwakel, Holland. The varietal denomination of the new variety is 'Ruioran'. The new variety was isolated and asexually reproduced by budding in De Kwakel, Holland.

SUMMARY OF THE INVENTION

Among the novel characteristics possessed by this new variety which distinguish it from its parents and all other varieties of which I am aware are its attractive orange yellow flowers of good form borne on a floriferous plant with long stems and suitable for production of cut flowers under glass. The new variety has been reproduced through propagation by cuttings, grafting, budding and micropropagation.

Asexual reproduction by budding of the new variety as performed in De Kwakel, Holland shows that the foregoing and other distinguishing characteristics come true to form and are established and transmitted through succeeding propagations.

DESCRIPTION OF THE NEW VARIETY

The following is a detailed description of the new variety, with color terminology in accordance with The Royal Horticultural Society Colour Chart (R.H.S.C.C.) and horticultural terminology in accordance with standard terminology used in UPOV-approved horticultural guideline. The terminology used in color descriptions herein refers to plate numbers in the aforementioned color chart. Phenotypic expression may vary depending upon growing conditions under different climate, soil, and cultivation conditions.

Parentage: Seed and pollen parents are seedlings.
Class: Hybrid Tea.

As can be seen in Sheet 2 there is shown a new shoot and green bud, 1; compound three, five and seven leaflet leaves though only 6 leaflets are shown, one was broken and removed, 2, 3 and 4, respectively; a stem, 5; buds, 6, 7 and 8; a flower, 9, and flower stems 10, 11 and 12, with reproductive organs displayed.

The following further horticultural description is based on observations made of specimens grown under glass in De Kwakel, Holland.

Flower

Blooming habit: Nearly continuous.

A. Bud:

(1) *Size*.—Medium, about 3 to 4 cm long and about 3 cm wide.

(2) *Form*.—Ovate (shape of longitudinal section just before separation of sepals); urn-shaped after sepals part.

(3) *Color*.—As sepals divide, near 32A to 32B, with yellow toward point of attachment.

(4) *Sepals*.—Medium to long, some foliated, medium green; undersurface near 144A, upper surface near 59B with greenish tonality near 146B.

(5) *Peduncle*.—Long, erect, very strong. Color near 137A to near 137B.

B. Bloom:

*Flower*.—Medium; viewed from above — star-shaped; viewed from side — (a) upper part of fully opened flower, flattened convex; (b) lower part of fully opened flower, flat.

(1) *Size*.—Average size when fully expanded — about 7 to 10 cm.

(2) *Borne*.—Singly, one to a stem.

(3) *Form*.—Exhibition type, somewhat flat top, spiral imbricated, outer petals reflex to points and inner petals curl under.

(4) *Petalage*.—About 24.

(5) *Color*.—After sepals part and petals unfurl color of petal undersurface visible is near 32A to 32B with yellow at point of petal attachment, lightening to near 23A to 23C; as flower opens color remains the same but on petal top surface petalage near 33B to 33C becomes visible. Open flowers appear near 23A to near 19A approaching near 26B. Overall tonality from a distance is attractive orange yellow to yellow blend.

(6) *Peduncle*.—Few hairs or prickles, near 138A to 138B; about 12 cm.

(7) *Fragrance*.—Very weak to weak.

(8) *Length of stem**.—About 80 cm from last cuat.

(9) *Production**.—About 230 blooms/$m^2$/year.

*Average, actual depends on circumstances of cultivation

*Petals*.—(1) Texture: Crisp. (2) Appearance: Inside velvety and outside satiny. (3) Form and size: Broad, medium, petals reflex to points. (4) Arrangement: Regularly arranged, imbricated. (5) Petaloids: About 10. (6) Lasting quality: Long-lasting quality on plant and after cutting; vase life varies from 8 to 18 days and blooms on plant last about 16 days after which petals tend to drop.

Reproductive organs

A. Stamens, filaments and anthers:
*Arrangement and color*.—Regularly arranged around styles; color of filaments — orange yellow.
B. Pollen:
*Color*.—Orange yellow.
C. Styles: Long, stigma above mouth of receptacle, yellow.
D. Stigmas: Yellow, positioned below anthers
E. Hip: Funnel-shaped; medium seed vessel at petal fall; green to orange, about 2 cm.

Plant

A. Form: Narrow, bushy, average disease resistance, may be subject to powdery and downey mildew; plant height about 1.8 meters, plant width about 0.5 meters.
B. Growth: Vigorous, medium length and width.
C. Foliage: Compound 3, 5 and 7 leaflets.
(1) *Size*.—Small to medium about 14 to 17 cm.
(2) *Quantity*.—Abundant.
(3) *Color*.—Juvenile foliage — red purple to reddish brown; top near 187A underside near 177A; weak anthocyanin coloration, (shoot about 20 cm long); mature leaf color—upper side near 139A, under side near 197A.
(4) *Shape*.—Elliptic.
(5) *Texture*.—Upper side is medium glossy; underside is matte.
(6) *Edge*.—Serrate.
(7) *Serration*.—Serrate to double serrate.
(8) *Leaf stem*.—Color — near 147A to 147B.
(9) *Stipules*.—Variable, short to long, variable margins, medium green with dark edge and/or tips, distinct auricle.
(10) *Leaflets*.—Cross section — slight concave: medium to strong undulation of margin; terminal leaflet blade medium long and wide; terminal leaflet 3 — leaflet leave, 8 to 9 cm; 5 — leaflet leave, 6 to 7 cm; 7 — leaflet leaf, 4 to 5 cm, wedge-shaped base
D. Wood:
(1) *New wood*.—Color — young shoots have weak anthocyanin; coloration — bronze red purple to reddish brown; coloration near 165A.
(2) *Old wood*.—Color — near 147A to 147B.
E. Prickles (thorns):
(1) *Prickles*.—Present; quantity (main stalk) — very few; shape of lower side — concave; Length — short prickles, few to medium; long prickles few; Position — irregular.

What is claimed is:

1. A new and distinct variety of rose plant of the hybrid tea rose class, substantially as shown and described.

* * * * *

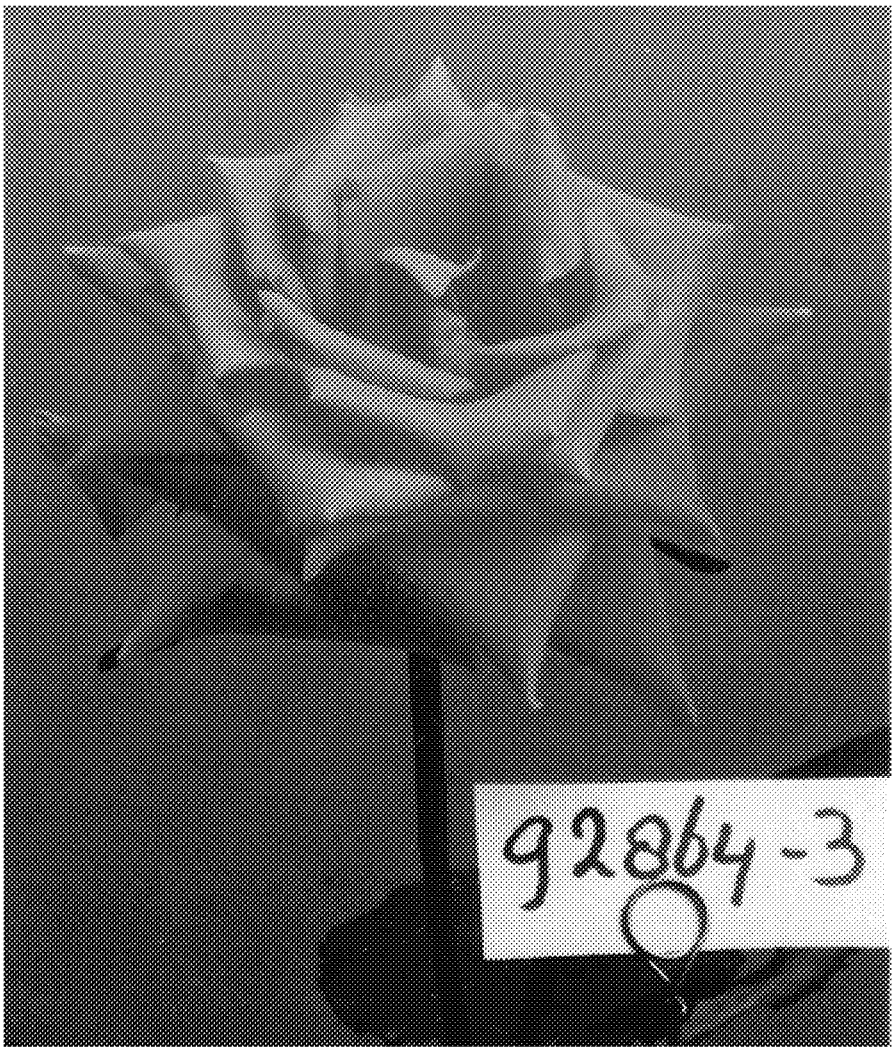
92864-3

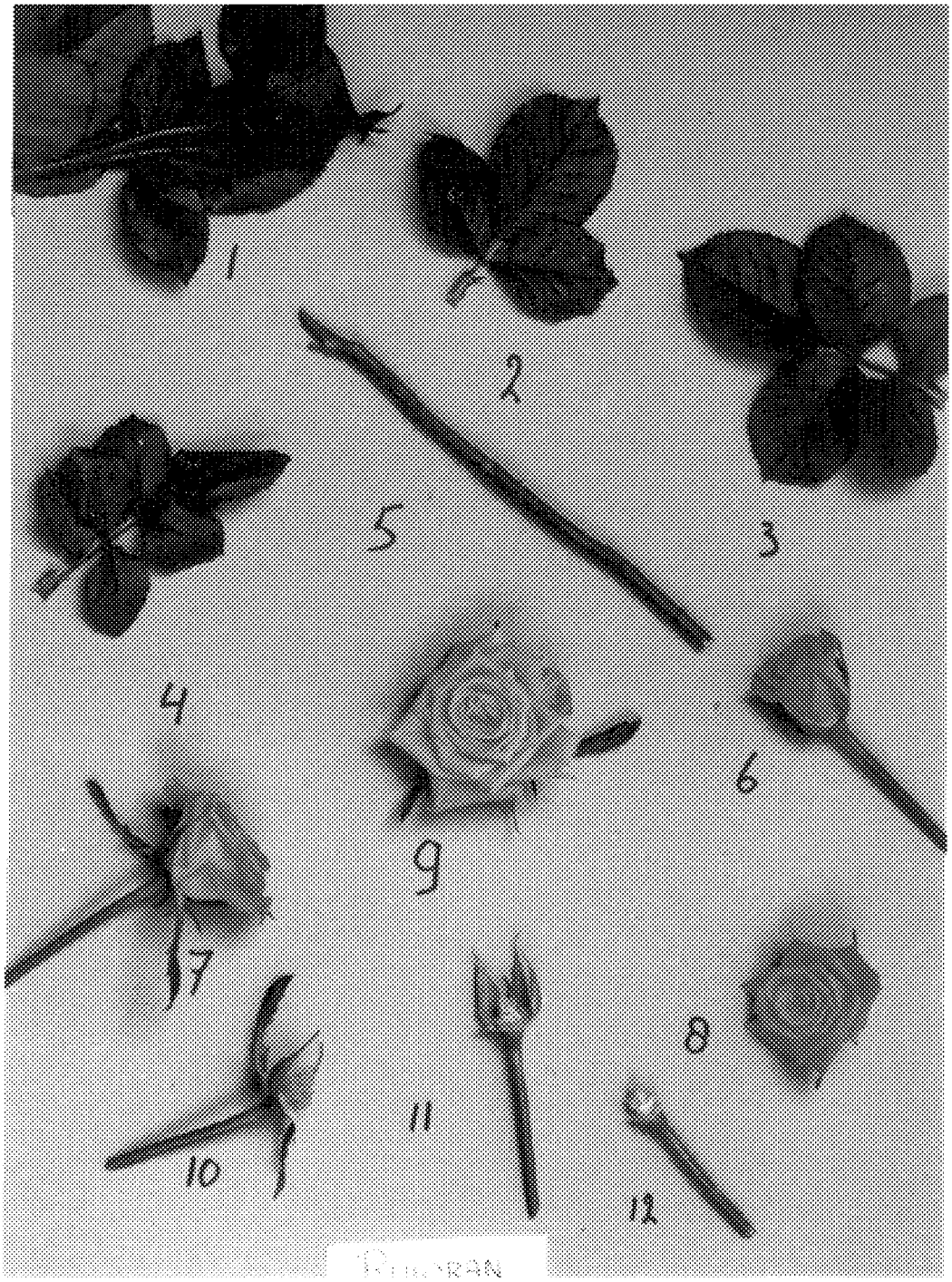
1
2
3
4
5
6
7
8
9
10
11
12